United States Patent
Smith et al.

(12) 
(10) Patent No.: US 6,358,952 B1
(45) Date of Patent: *Mar. 19, 2002

(54) COMBINATION OF BENZOQUINAZOLINE ANTIFOLATES AND PROTECTING AGENTS

(75) Inventors: Gary Keith Smith, Raleigh; David Stanley Duch, Cary; Robert Ferone, Raleigh, all of NC (US); Arthur Koch, Bloomington, IN (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/448,393
(22) PCT Filed: Dec. 21, 1993
(86) PCT No.: PCT/GB93/02611
§ 371 Date: Jun. 6, 1995
§ 102(e) Date: Jun. 6, 1995
(87) PCT Pub. No.: WO94/14448
PCT Pub. Date: Jul. 7, 1994

(30) Foreign Application Priority Data

Dec. 23, 1992 (GB) .............................. 9226842

(51) Int. Cl.$^7$ ...................... A61K 31/495; A61K 31/50; A61K 31/505
(52) U.S. Cl. ........................................ 514/249; 514/267
(58) Field of Search ................................ 514/249, 267

(56) References Cited

U.S. PATENT DOCUMENTS 5,217,974 A 6/1993 Grindey et al. ............. 514/260

FOREIGN PATENT DOCUMENTS

EP 0 505 640 A1 9/1991 ..................... 37/64
WO WO 91/19700 12/1991 ................... 239/70

OTHER PUBLICATIONS

Bos et al., Experient, 25(8), 811–12 Abstract Only, 1969.*
Goodman, et al., "Folic Acid Analogs" *The Pharmological Basis of Therapeutics*, Chap. 55, pp. 1263–1267.
R, Arky, *Physicians Desk Reference*, pp. 720–722.
H.M. Said and D. Hollander, "Inhibitory Effect of Bile Salts on the Enterohepatic . . . ," Cancer Chemother Pharmacol, (1986) vol. 16, pp. 121–124.
G.B. Grindey et al., "Reversal of the Toxicity but not the Antitumor Activity of . . . " Proc. Amer. Assoc. for Cancer Res., Abstr. 1921, (Mar. 1991), vol. 32, p. 324.
K. Shrestha and D.M. Miller, "Specific Inhibition of c–myc Transcription by a Triplex Forming Acridine–oligonuclide Conjugate . . . ," Proc. Amer. Assoc. for Cancer Res., Abstr. 2422, (Mar. 1991), vol. 32, p. 407.
A.R. Khokhar et al., "Development of Liposomes–encapsulated Lipophilic . . . " Proc. Amer. Assoc. for Cancer Res., Abstr. 2432, (Mar. 1991), vol. 32, p. 409.
T.R. Jones et al., "Quinazoline Antifolates Inhibiting Thymidylate Synthase: Benzoyl Ring Modification," J. Med. Chem. (1986), vol. 29, No. 4, pp. 468–472.
International Search Report for PCT/GB93/02611.
Bos et al., "Induction of Morphlogical Aberrations by Enzyme Inhibition in *Drosphila melanogaster*:", 25 (8), 811–812.
Silber, J. et al., Dihydrofolate reductase activity and resistance to aminopterin in various species of *Drosphila*, Mol. Gen Genet, 200(1): 92–95 1985.
Silber, J. et al., Vestigal mutants of *Drosphila melanogaster* live better in the presence of aminopterin: Increased level of dihydrofolate reductase in a mutant, Mol Gen Genet (1989) 2:18: 475–480.
Galivan et al., "The Characteristics and Consequences of Folate Depletion in Hepatoma Cells in Vitro by Inhibition of Dihydrofolate Reductase", *Advances in Enzyme Regulation*, pp. 209–217, 1989.
ABPI Data Sheet Compendium, *Datapharm Publications Limited*, , pp. 838–840, 1990.
Beardsley et al., "A New Folate Antimetabolite, 5, 10–Dideaza–5,6,7,8–tetrahydrofolate Is a Potent Inhibitor of de Novo Purine Synthesis", *The Journal of Biological Chemistry*, vol. 264, No. 1, pp. 328–333, Jan. 5, 1989.
Morgan, et al., "The Effect of Folic Acid Supplementation on the Toxicity of Low–Dose Methotrexate in Patients with Theumatoid Arthritis", *Athritis and Rheumatism*, vol. 33, No. 1, Jan. 1990, pp. 9–18.
Pavlotsky, et al., "Selective Protection of the Gastrointestinal Tract Against Methotrexate in the Treatment of Patients with Trophoblastic Tumors", *Cancer Treatment Reports*, vol. 61, No. 5, Aug. 1977, pp. 895–897.
Goldin, et al., "Estimation of the Antileukemic Potency of the Antimetabolite Aminopterin, Administered Alone and in Combination with Citrovorum Factor or Folic Acid", *Cancer Research*, , pp. 843–850, May 1959.
Kane, et al., "Biology of Disease Role of Folate Binding Proteins in Folate Metabolism", *Laboratory Investigation*, vol. 60, No. 6, pp. 737–746, 1989.
Jackson, "The Biochemical Basis for Methotrexate Cytotoxicity", *Folate Antagonists as Therapeutic Agents*, vol. 1, Chapter 8, pp. 289–315, 1984.

(List continued on next page.)

Primary Examiner—Jerome D. Goldberg
(74) Attorney, Agent, or Firm—John L. Lemanowicz

(57) ABSTRACT

The use of a protecting agent, for example a folate derivative such as folic acid or leucovorin, in combination with a non-competitive folic acid analogue, for example benzoquinazoline derivatives, for use in reducing the side effects associated with the administration of such non-competitive folic acid analogues, and pharmeceutical formulations comprising such combinations are disclosed.

11 Claims, No Drawings

OTHER PUBLICATIONS

*Physicians' Desk Reference*, 45th Edition, Medical Economics Company Inc., pp 776, 1185–1189, 1991.

Beardsley, "Proceedings of the Ninth International Symposium on Pteridines and Folic Acid Derivatives Chemical, Biological and Clinical Aspects, Zurich, Switzerland Sep. 3–8, 1989, pp. 1001–1008", *Chemistry and Biology of Pteridines*, 1989.

Pizzorno et al, Proceedings of the Ninth International Symposium on Pteridines and Folic Acid Derivatives Chemical, Biological and Clinical Aspects, Zurich, Switzerland Sep. 3–8, 1989, pp. 1031–1034, *Chemistry and Biology of Pteridines*, 1989.

* cited by examiner

COMBINATION OF BENZOQUINAZOLINE ANTIFOLATES AND PROTECTING AGENTS

The present invention relates to novel combinations of non-competitive folic acid analogues with protecting agents, and to methods of treatment using these combinations.

European Patent Application 0505640 provides a method for improving the therapeutic utility of GAR-transformylase inhibitors and other antifolates by co-administering a folate binding protein binding agent to the host undergoing treatment.

Thymidylate synthase is an enzyme catalysing the terminal step in the de novo synthesis of thymidylate required for DNA synthesis. It has been postulated that inhibitors of this enzyme may be expected to have anti-tumour activity and it has been reported (Jones et al, J. Med. Chem. 1986, 22, 468) that the in-vivo antitumour activity of $N^{10}$-propargyl-5,8-dideazafolic acid arises solely from its inhibitory effect on this enzyme.

PCT publication WO/91/19700 discloses the compound of the formula (I)

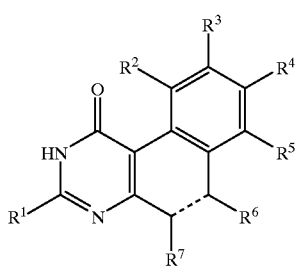

(I)

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, a group $S(O)_n R^8$ wherein n is the integer 0. 1 or 2 and $R^8$ is halo or is $C_{1-4}$ alkyl or a group $NR^9 R^{10}$ wherein $R^9$ and $R^{10}$ are both hydrogen;

a group $NR^{11}R^{12}$ wherein $R^{11}$ and $R^{12}$ are the same or different and each is hydrogen or $C_{1-4}$ alkyl, a group $OR^{13}$ wherein $R^{13}$ is hydrogen or $C_{1-4}$ alkyl optionally substituted by halo;

a $C_{1-4}$ aliphatic group optionally substituted by a group $OR^{14}$ or $NR^{14}R^{15}$ wherein $R^{14}$ and $R^{15}$ are the same or different and each is hydrogen or $C_{1-4}$ alkyl;

or two of $R^2$ to $R^5$ are linked together to form a benzo group, or one of $R^2$ to $R^5$ is a group —X—Y—$R^{16}$ wherein X is $CH_2$, $NR^{17}$, CO or $S(O)_m$ and m is 0,1 or 2 and $R^{17}$ is hydrogen or a $C_{1-4}$ aliphatic group and Y is $CH_2$, O, $NR^{17'}$ or $S(O)_{m'}$ wherein m' is 0,1 or 2 and $R^{17'}$ is hydrogen or a $C_{1-4}$ aliphatic group provided that X and Y are only the same when each is $CH_2$, or —X—Y— is a group —O—, —$NR^{17}$—, —CH=CH— or —N=N— wherein $R^{17}$ is as hereinbefore defined, $R^{16}$ is a $C_{1-4}$ aliphatic group or a 5- or 6-membered aromatic ring optionally substituted by a group $R^{18}$ at a position at least one carbon atom removed from that linked to Y, the 5- or 6-membered ring being optionally further substituted by a halo atom; and $R^{18}$ is halo, $C_{1-4}$ alkoxy, nitro, nitrile, $C_{1-4}$ alkyl optionally substituted by halo, halo or a group $COR^{19}$ wherein $R^{19}$ is hydroxy, $C_{1-4}$ alkoxy or $C_{1-6}$ alkyl optionally substituted by one or two carboxyl groups or $C_{1-12}$ esters thereof or $R^{19}$ is a group $NR^{20}R^{21}$ wherein $R^{20}$ and $R^{21}$ are the same or different and each is hydrogen or $C_{1-4}$ alkyl optionally substituted by hydroxy or $R^{19}$ is an amino acid group or an ester thereof in which the first nitrogen atom of the amino acid group may be linked to the 5- or 6-membered aromatic ring to form a further 5- or 6-membered heterocyclic ring or $R^{19}$ is an $C_{2-3}$ alkylene group linked to the 5- or 6-membered aromatic ring to form a further 5- or 6-membered ring;

$R^6$ and $R^7$ are the same or different and each is hydrogen, $C_{1-4}$ alkyl optionally substituted by hydroxy or $C_{1-4}$ alkoxy or together form a benzo group;

provided that at least one of $R^2$ to $R^7$ is other than hydrogen and that $R^4$ is not methoxy when $R^1$ is hydroxy or methyl;

is an inhibitor of the enzyme thymidylate synthase and has anti-tumour activity.

By the term halo is meant fluoro, bromo, chloro and iodo.

By the term $C_{1-4}$ aliphatic group is meant a $C_{1-4}$ alkyl, alkenyl, or alkynyl group.

By the term amino acid group is meant naturally occurring amino acids.

Preferred amino acid groups include glycine, glutamic acid and polyglutamic acid groups.

When the amino acid group is linked to the 5- or 6-membered aromatic ring, this is via a carbon atom of the aromatic ring adjacent to carbon to which $COR^{19}$ is attached.

Preferably the dotted line is a double bond.

Suitable substituents for the aromatic ring $R^{16}$ include halo, $C_{1-4}$ alkyl and $C_{1-4}$ alkoxy each optionally substituted by one to five halo atoms. Most suitably there are one or two substituents selected from fluoro, chloro, methyl, trifluoromethyl and methoxy, and preferably fluoro, or no substituents on the aromatic ring. In one preferred embodiment, —X—Y—$R^{16}$ is a group

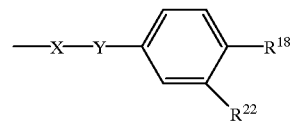

wherein $R^{18}$ is as hereinbefore defined and preferably a group $COR^{19}$ as hereinbefore defined and $R^{22}$ is hydrogen or fluoro.

In a further preferred embodiment X—Y—$R^{16}$ is a group

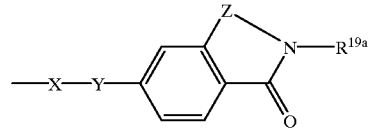

wherein $H_2 NR^{19a}$ is a glutamic or polyglutamic acid group and Z is $CH_2$, S or O.

Suitably, $R^1$ is an amino group optionally substituted by one or two methyl or ethyl groups or $R^1$ is a methyl or ethyl group. Preferably $R^1$ is an amino or methyl group.

Suitably, at most only three, and preferably at most only two, of $R^2$ to $R^5$ are other than hydrogen and each is independently selected from hydrogen, halo, hydroxy, nitro.

$C_{1-3}$ alkyl optionally substituted by hydroxy or $C_{1-2}$ alkoxy, $C_{1-3}$ alkoxy, amino optionally substituted by one or two methyl or ethyl groups, or a group $S(O)_n R^{23}$ wherein n is 0, 1 or 2 and $R^{23}$ is a $C_{1-4}$ alkyl group or an amino group optionally substituted by one or two methyl or ethyl groups, or one of $R^2$ to $R^5$ is a group —X—Y—$R^{24}$ where $R^{24}$ is a group

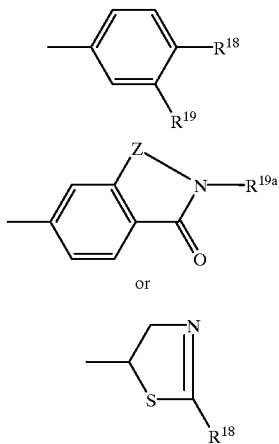

or wherein $R^{18}$, $R^{19a}$, $R^{22}$ and Z are as hereinbefore defined. In one preferred embodiment $R^{18}$ is nitro or a group

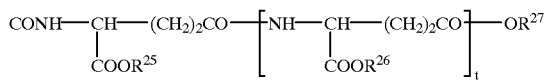

wherein $R^{25}$, $R^{26}$ and $R^{27}$ are the same or different and each is hydrogen or a $C_{1-4}$ alkyl group and t is an integer from 0 to 6. Preferably $R^{25}$, $R^{26}$ and $R^{27}$ are hydrogen and t is 0. Preferably Z is $CH_2$ or S.

Preferably one of $R^2$ to $R^5$ is a group —X—Y—$R^{24}$ as hereinbefore defined. Preferably $R^3$ is a group —X—Y—$R^{24}$.

Suitably $R^6$ and $R^7$ are the same or different and each is hydrogen, methyl, ethyl or methyl substituted by bromo, hydroxy or methoxy. Preferably $R^7$ is hydrogen and $R^6$ is methyl.

Preferably —X—Y— is a group —$SO_2NR^{17}$— or $CH_2NR^{17}$ wherein $R^{17}$ is as hereinbefore defined.

Suitably $R^{17}$ is hydrogen or a $C_{1-4}$ alkyl or alkenyl group and preferably $R^{17}$ is hydrogen or methyl.

A further group of compounds of the formula I is that of the formula (II)

(II)

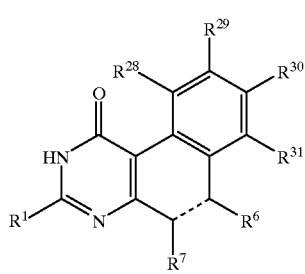

or a salt thereof, wherein $R^1$, $R^6$, $R^7$ and the dotted line are as hereinbefore defined and $R^{28}$ to $R^{31}$ are the same or different and each is selected from hydrogen, halo, nitro, a group $S(O)_n R^8$, a group $NR^{11}R^{12}$, a group $OR^{13}$, or a $C_{1-4}$ aliphatic group optionally substituted by a group $OR^{14}$ or $NR^{14}R^{15}$ wherein $R^8$, $R^{11}$, $R^{12}$, $R^{13}$, $R^{14}$ and $R^{15}$ are as hereinbefore defined, provided that $R^{28}$ to $R^{31}$ are not all hydrogen and that $R^{30}$ is not methoxy wherein $R^1$ is hydroxy or methyl.

A preferred group of compounds of the formula (I) is that of the formula (III):

(III)

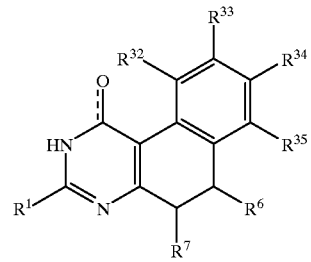

or a salt thereof, wherein $R^1$, $R^6$ and $R^7$ are as hereinbefore defined and $R^{32}$ to $R^{35}$ are the same or different and one is a group X—Y—$R^{16}$ and the others are the same or different and each is selected from hydrogen, halo, nitro, a group $S(O)_n R^8$, a group $NR^{11}R^{12}$, a group $OR^{13}$ or a $C_{1-4}$ aliphatic group optionally substituted by a group $OR^{14}$ or $NR^{14}R^{15}$, wherein X, Y, $R^8$, $R^{11}$, $R^{12}$, $R^{13}$, $R^{14}$, $R^{15}$ and $R^{16}$ are as hereinbefore defined.

A further preferred group of compounds of the formula (I) is that of the formula (IV):

(IV)

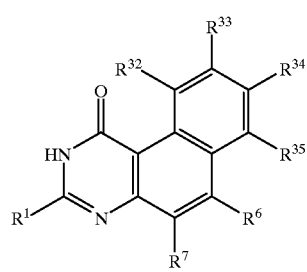

wherein $R^1$, $R^6$, $R^7$ and $R^{32}$ to $R^{32}$ are as hereinbefore defined.

Preferably $R^{33}$ is a group X—Y—$R^{16}$ as hereinbefore defined.

Preferred compounds of the formula (I) include:
3-Amino-9-bromobenzo[f]quinazolin-1(2H)-one
3-Amino-9-ethynylbenzo[f]quinazolin-1(2H)-one
N-(4-((3-Amino-1,2,5,6-tetrahydro-1-oxobenzo[f]quinazolin-9-yl)sulfonamido)benzoyl)-L-glutamic acid
N-(4-((1,2,5,6-tetrahydro-3-methyl-1-oxobenzo[f]quinazolin-9-yl)-sulfonamido)benzoyl)-L-glutamic acid
N-(4-((1,2-Dihydro-3-methyl-1-oxobenzo[f]quinazolin-9-yl)sulfonamido)benzoyl)-L-alutamic acid
N-(4-(((1,2-Dihydro-3-methyl-1-oxobenzo[f]quinazolin-9-yl)methyl)amino)-2-fluorobenzoyl)-L-glutamic acid
N-(4(((1,2-Dihydro-3-methyl-1-oxobenzo[f]quinazolin-9-yl)methyl)amino)benzoyl)-L-glumatic acid
(S)-2-(5-(((1,2-Dihydro-3-methyl-1-oxobenzo[f]quinazolin-9-yl)methyl)amino-1-oxo-2-isoindolinyl) glutaric acid 9-((4-Acetylanilino)methyl)-3-methylbenzo[f]
quinazolin-1(2H)-one 3-Methyl-9-((4-nitroanilino)methyl)benzo[f]quinazolin-1
(2H)-one N-(4-(((3-Amino-1,2-dihydro-1-oxobenzo[f]quinazolin-
9-yl)methyl)amino)benzoyl)-L-glutamic acid 3-Amino-9-((4-nitroanilino)methyl)benzo[f]quinazolin-1
(2H)-one 9-((4-Acetylanilino)methyl)-3-aminobenzo[f]quinazolin-
1(2H)-one (RS)-2-(2-(4-(((1,2-Dihydro-3-methyl-1-oxobenzo[f]
quinazolin-9-yl)methyl)amino)phenyl)-2-oxoethyl)
glutaric acid Ethyl-4-(4-(((1,2-dihydro-3-methyl-1-oxobenzo[f]
quinazolin-9-yl)methyl)amino)phenyl)-4-oxobutyrate 4-(4-(((1,2-Dihydro-3-methyl-1-oxobenzo[f]quinazolin-
9-yl)methyl)amino)phenyl)-4-oxobutyric acid N-(4-(((1,2-Dihydro-3-methyl-1-oxobenzo[f]quinazolin-
9-yl)methyl)amino)-2-fluorobenzoyl)glycine Ethyl N-(4-(((1,2-Dihydro-3-methyl-1-oxobenzo[f]
quinazolin-9-yl)methyl)amino)-2-fluorobenzoyl)
glycinate Certain compounds of the formula (I) contain asymmetric carbon atoms and are, therefore, capable of existing as optical isomers. The individual isomers and mixtures of these are included within the scope of the present invention.

It has now been found that the compounds of formula (I) can be used in combination with a protecting agent described hereinafter to prevent or decrease unwanted side effects of these compounds.

The present invention relates to the administration of the compounds of formula (I) in combination with a protecting agent which blocks the intestinal toxicity of the compounds of formula (I) without blocking their activity. Suitable protecting agents are folates, for example, folic acid, tetrahydrofolate, 5-formyltetrahydrofolate (leucovorin) or 5-methyltetrahydrofolate. Other protecting agents include thymine or thymidine. The protecting agent may be administered as an oral formulation. It is within the scope of the invention to administer the protecting agent before, during or after the administration of a compound of formula (I). Preferably, the protecting agent will be given slightly before administration of a compound of formula (I), i.e. between 15 minutes and one hour before the compound of formula (I).

The present invention also relates to combination therapy comprising the administration of non-competitive folic acid analogues in combination with protecting agents as defined above. This allows the use of the non-competitive folic acid analogues at higher doses than could be used in the absence of the protecting agent as defined above, and therefore higher, more potent doses can be achieved while minimizing host toxicity. The presence of the protecting agent reduces the toxicity of the non-competitive folic acid analogues at the doses utilized in the absence of the protecting agent (i.e. less toxicity at the same dose in the presence of a protecting agent).

Non-competitive folic acid analogues are defined as structural analogues of folic acid (including but not limited to the benzoquinazoline compounds of formula I, e.g., compounds of example 1 or 2) expressing classical non-competitive inhibition kinetics (vs. the folate substrate) on the target enzyme (e.g., thymidylate synthase, glycineamide ribonucleotide transformylase or dihydrofolate reductase). Alternatively, the non-competitive inhibitors of the present invention are defined as structural analogues of folic acid (as defined above) which retain their tumour cell kill in the presence of the folate protecting agents defined above, on the target enzyme. The non-competitive inhibitor may been given as an intravenous or intraperitoneal bolus or infusion and the protecting agent may be given as an intravenous or intraperitoneal bolus infusion or as an oral formulation. For a definition of classical non-competitive inhibition see I. H. Segal (1975) *Enzyme kinetics*, John Wiley and Sons, which is incorporated herein by reference.

More specifically, protecting agents selected from folic acid, tetrahydrofolate, 5-formyltetrahydrofolate (leucovorin) or 5-methyltetrahydrofolate can block the intestinal toxicity of compounds of formula (I) without blocking their anti-tumor activity.

Preferably, the non-competitive, folic acid analogue (i.e. non-competive inhibitor) is a compound of formula (I) and the protecting agent is folic acid or 5-formyltetrahydrofolate. More preferably, the non-competitive, folic acid analogue (non-competitive inhibitor) is a compounds selected from (S)-2-(5-(((1,2-dihydro-3-methyl-1-oxobenzo(f)quinazolin-9-yl)methyl)amino)-1-oxo-2-isoindolinyl)glutaric acid, N-(4-(((1,2-dihydro-3-methyl-1-oxobenzo(f)quinazolin-9-yl)methyl)amino)-2-fluorobenzoyl)-L-olutamic acid, or N-(4-((1,2,5,6-tetrahydro-3-methyl-1-oxobenzo(f)quinazolin-9-yl)sulfonamido)benzoyl)-L-glutamic acid and the protecting agent which is used in combination is folic acid or 5-formyltetrahydrofolate. Most preferbly, the compound (S)-2-(5-(((1,2-dihydro-3-methyl-1-oxoxbenzo(f)quinazolin-9-yl)methyl)amino)-1-oxo-2-isoindolinyl) glutaric acid is utilized in combination with folic acid or 5-formyltetrahydrofolate.

The salts of the compounds of the present invention can also be used in combination with the protecting agent or salts thereof.

Suitable salts of the compounds of the present invention or of the protecting agents may comprise acid addition salts derived from an amino group or anionic species derived from a compound of formula (I) or protecting agent, for example when this is substituted by a carboxy group, and a cation. In both types of salts, the therapeutic activity resides in the moiety derived from the compounds defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycollic, gluconic, succinic and methanesulphonic and arylsulphonic, for example p-toluenesulphonic, acids. Examples of salts comprising an anionic species derived from a compound of formula (I) and a cation include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylamino-ethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the pharmaceutically unacceptable salts are also useful in being convertible to the pharmaceutically acceptable salts by techniques well known in the art.

The route by which the compound or salt of the present invention is administered to the animal may be oral, topical, parenteral (including subcutaneous, intradermal, intramuscular, intravenous or rectal). If the compound or salt is presented in the form of a pharmaceutical formulation, which is preferred, then the actual formulation employed will of course depend on the route of administration elected by the physician or veterinarian. For example, if oral administration is preferred, then the pharmaceutical formulation employed is, preferably, one which is suitable for such a route.

A therapeutically effective amount of a compound or salt of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a non-competitive folic acid analogue of the present invention (as described hereinbefore) to be used in combination with a protecting agent (as described hereinbefore) for the treatment of neoplastic growth, for example colon or breast carcinoma will generally be in the range of 0.1 to 100 mg/kg body weight of recipient (mammal) per day and more usually in the range of 1 to 50 mg/kg body weight per day. Thus, for a 70 kg adult mammal, the actual amount per day would usually be from 70 to 3500 mg and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

An effective amount of a compound of the present invention for the treatment of disorders of the immune system (e.g. rheumatoid arthritis and tissue rejection) and related diseases such as psoriasis, will generally be in the range of 0.5–10 mg/kg body weight of recipient (mammal) per day. Thus for a 70 kg adult human, the actual amount per day would usually be from about 5–700 mg per day and this amount may be given in a single dose per day or more usually dosing would be intermittent e.g. 12 hourly intervals or weekly. An effective amount of a salt of the present invention may be determined as a proportion of the effective amount of the compound per se.

An effective amount of a compound of the present invention for the treatment of bacterial and fungal infections is in the range of 0.1–100 mg/kg bodyweight of recipient (mammal) per day and preferably in the range of 1–50 mg/kg body weight per day. Thus, for a 70 kg adult mammal, the actual amount per day is from 70–3500 mg and this amount may be given in a single dose per day or more preferably in a number (such as two, three, four, five or six) of sub-doses per day such that the total daily dose is the same. An effective amount of a salt of the present invention may be determined as a proportion of the effective amount of the compound per se.

An effective amount of a protecting agent (e.g., folic acid) of the present invention for use in combination with a non-competitive, folic acid analogue (including but not limited to the compounds of the present invention as described herein) is in the range of 1–300 mg/kg bodyweight of recipient (mammal) per day and preferably in the range of 5–50 mg/kg body weight per day. Thus, for a 70 kg adult mammal, the actual amount per day is from 350–3500 mg and this amount may be given in a single dose per day or more preferably in a number (such as two, three, four, five or six) of sub-doses per day such that the total daily dose is the same.

The treatment of neoplastic growth with a compound of the present invention may at times require the administration to the animal of an antidote or rescue agent, e.g. thymidine.

The compounds, per se, of the present invention which can be used in combination with a protecting agent as described herein include, but are not limited to, those disclosed in PCT publication WO/91/19700. The protecting agents of the present invention are readily available and well known to those skilled in the art.

Whilst it is possible for the compounds or salts of the present invention to be administered as the raw chemical, it is preferred to present them in the form of a pharmaceutical formulation.

Accordingly, the present invention further provides a pharmaceutical formulation, for medicinal application, which comprises a compound of the present invention and a protecting agent or pharmaceutically acceptable salts thereof, as hereinbefore defined, in combination with one or more pharmaceutically acceptable carriers therefor, and optionally one or other therapeutic agredients.

The pharmaceutical formulation may optionally contain other therapeutic agents that may usefully be employed in conjunction with the compound or salt of the present invention, for example a pyrimidine nucleoside transport inhibitor that is capable of enhancing the antineoplastic activity of the compounds and salts of the presents invention. The expression "pharmaceutically acceptable" as used herein in relation to the carrier is used in the sense of being compatible with the compound or salt of the invention employed in the formulation and with any other therapeutic agent that may be present, and not being detrimental to the recipient thereof. The carrier itself may constitute one or more excipients conventionally used in the art of pharmacy that enable the compound or salt of the present invention and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration although the most suitable route will probably depend upon, for example, the condition and identity of the recipient. The formulations may conveniently be presented in unit dosage form and may be prepared by any of the methods will known in the art of pharmacy. All methods include the step of bringing into association the active ingredient, i.e., the compound or salt and protecting agent of the present invention, with the carrier.

In general, the formulations are prepared by uniformly and intimately bringing into association the active ingredients with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient, as a powder or granules; as a solution or a suspension in an aqueous liquid or a non-aqueous liquid such as a syrup, elixir or a draught, or as an oil-in water liquid emulsion or a water-in-oil liquid emulsion. The formulation may also be a bolus, electuary or paste.

Generally, a tablet is the most convenient pharmaceutical formulation suitable for oral administration. A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqeuous sterile injection solutions which may contain, for example, an anti-oxidant, a buffer, a bacteriostat and a solution which renders the composition isotonic with the blood of the recipient, and aqueous and non-aqueous sterile suspensions which may contain, for example, a suspending agent and a thickening agent. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

Compounds and salts of formula (I) have anti-neoplastic activity in the human colon SW480 adenocarcinoma cell culture cytotoxicity tests in which representative compounds of the present invention have been shown to be active, and in human breast MCF7 adenocarcinoma cell culture. It has thus been established that compounds of the present invention are able to inhibit neoplastic growth. Therefore, compounds and salts of the present invention are of use in medicine and in particular in the treatment of neoplastic growth, including solid tumours such as melanoma breast and colon tumours in mammals. Accordingly, the present invention yet further provides a method for the treatment of susceptible malignant tumours and leukemia in a animal, e.g. a mammal, which comprises administering to the animal a therapeutically effective amount of a compound or salt of the present invention in combination with a protecting agent. In the alternative, there is also provided a compound or salt of the present invention in combination with protecting agent. In the alternative, there is also provided a compound or salt of the present invention in combination with a protecting agent for use in medicine and in particular for use in the treatment of a neoplastic growth, e.g. malignant tumours.

The present invention also provides the use of a compound of formula (I) or a salt thereof in combination with a protecting agent for the maufacture of a medicament for the treatment of neoplastic growth.

The animal requiring treatment with a compound or salt of the present invention in combination with a protecting agent is usually a mammal, such as a human being.

The following examples illustrate the preparation and pharmacological properties of representative compounds which are useful in the present invention and which demonstrate the invention. These examples are illustrations only and should not be construed as limiting or narrowing the scope of the invention.

EXAMPLE 1

(S)-2-(5-(((1,2-Dihydro-3-methyl-1-oxobenzo[f] quinazolin-9-yl)methyl)amino)-1-oxo-2-isoindolinyl)glutaric Acid (Compound A)

A. Diethyl (S)-2-(4-Nitrophthalimido)glutarate

Diisopropylethylamine (24 ml, 0.138 mole) (Aldrich) was added to a suspension of 4-nitrophthalic anhydride (25 g, 0.13 mole) (Tokyo Kasei) and L-glutamic acid diethyl ester hydrochloride (35 g, 0.146 mole) (Aldrich) in toluene (130 ml). The reaction mixture was stirred at reflux utilizing a Dean-Stark trap for 2.5 hours. After cooling, the solution was diluted with diethyl ether (300 ml), washed with water (75 ml), saturated $NaHCO_3$ solution (50 ml), dried ($MgSO_4$), and concentrated in vacuo at 70° C. to give diethyl (S)-2-(4-nitrophthalimido) glutarate as an oil that solidified to a white solid on standing (35.8 g). M.P.=65.5–66.5° C.

B. Diethyl (S)-2-(4-Aminophthalimido)glutarate

A suspension of diethyl (S)-2-(4-nitrophthalimido) glutarate (35.6 g, 94.1 mmol) and 10% palladium on carbon (0.5 g) (Aldrich) in ethanol (200 ml) was shaken under a hydrogen atmosphere (40–50 psi) for 26 hours. The solution was filtered through celite and concentrated in vacuo. The residue was purified by chromatography on silica gel (250 g) eluting with diethyl ether:hexane (4:1) to give diethyl (S)-2-(4-aminophthalimido)glutarate as a viscous yellow oil (29.1 g).

C. Diethyl (S)-2-(5-Amino-1-oxo-2-isoindolinyl)glutarate

A solution of diethyl (S)-2-(4-aminophthalimido) glutarate (10.5 g, 30.2 mmol) in ethanol (150 ml) was cooled in an acetonitrile/$CO_2$ bath. Concentrated HCl (25 ml) was added followed by 30 mesh granular Zn (10.5 g, 0.161 mole) (Fisher) when the internal temperature has reached −40° C. The reaction mixture was stirred 1.5 hours at this temperature and a further 1 hour at −10° C. The excess of Zn was filtered from the solution, 10% palladium on carbon (1.0 g) was added, and the solution shaken under hydrogen at (30–50 psi) overnight. The catalyst was removed by filtration through celite and the filtrate concentrated in vacuo. The residue was absorbed onto silica gel (15 g) and purified by chromatography on silica gel (440 g) eluting with ethyl acetate:methylene chloride (1:14 g).

D. 9-Bromomethyl-3-methylbenzo[f]quinazolin-1(2H)-one

To a hot solution of 3,9-dimethylbenzo[f]quinazolin-1(2H)-one (4.00 g, 17.9 mmol) in benzene (2000 ml) under nitrogen was added N-bromo-succinimide (4.00 g, 22.5 mmol). The reaction mixture was stirred just below reflux for 30 minutes, then at a gentle reflux for 30 minutes. The resulting suspension was allowed to cool for 2 hours, the solid filtered and dried at 70° C. under reduced pressure to give 9-bromomethyl-3-methylbenzo[f]quinazolin-1(2H)-one (4.32 g, 83% purity by NMR).

E. Diethyl (S)-2)-5-(((1,2-dihydro-3-methyl-1-oxobenzo[f] quinazolin-9-yl)methyl)amino)-1-oxo-2-isoindolinyl) glutarate A solution of crude 9-bromomethyl-3-methylbenzo[f] quinazolin-1(2H)-one (4.32 g), (S)-diethyl 2-(5-amino-1-oxo-2-isoindolinyl) glutarate (4.0g, 12 mmol), and $NaHCO_3$ (2.0 g, 24 mmol) in DMF (30 ml) was stirred under nitrogen at 105° C. for 1.5 hours. After cooling, acetic acid (1 ml, 17 mmol) was added, the reaction mixture transferred to a larger round bottom flask with ethanol, and then concentrated in vacuo onto silica gel (30 g). The absorbed material was purified by chromatography on silica gel eluting with methanol:methylene chloride (1:24) and then precipitation of the solid from methylene chloride (~20 ml) with ethyl acetate (~45 ml) and methanol (~5 ml). The white solid was filtered under nitrogen and dried under high vacuum to give diethyl (S)-2-(5-(((1,2-dihydro-3-methyl-1-oxobenzo[f]-quinazolin-9-yl)-methyl)amino)-1-oxo-2-isoindolinyl) glutarate (3.27 g).

F. (S)-2-(5-(((1,2-Dihydro-3-methyl-1-oxobenzo[f] quinazolin-9-yl)methyl)amino)-1-oxo-2-isoindolinyl)lutaric Acid A solution of diethyl (S)-2-(5-(((1,2-dihydro-3-methyl-1-oxo-benzo-[f]quinazolin-9-yl)methyl)amino)-1-oxo-2-isoindolinyl)glutarate (3.20 g, 5.75 mmol) in 0.2 N NaOH (140 ml) was stirred under nitrogen for 3 hours at room temperature. The solution was then slowly adjusted to pH3 with 1 N HCl and the resulting suspension allowed to stir briefly. The white solid was filtered under nitrogen, washed with water, and dried under high vacuum to give (S)-2-(5-(((1,2-dihydro-3-methyl-1-oxobenzo[f]quinazolin-9-yl) methyl)amino)-1-oxo-2-isoindolinyl)glutaric acid (2.85). $^1$H NMR (DMSO-d$_6$/D$_2$O, 300 MHz) δ: 1.86–2.34 (m, 4H, glu CH$_2$, CH$_2$), 2.44 (s, 3H, CH$_3$), 4.25 (very strongly coupled AB pair, 2H, glu NCH$_2$Ar), 4.58 (s, 2H, C$^9$-CH$_2$), 4.67–4.75 (m, 1H, glu CH), 6.69–6.77 (m, 2H, Ar), 7.37 (d, J=8 Hz, 1H, Ar), 7.59 (d, J=9 Hz, 1H, Ar), 7.64 (dd, J=8.2 Hz, 1H, Ar), 8.01 (d, J=8 Hz, 1H, Ar), 8.22 (d, J=9 Hz, 1H, Ar), 9.85 (s, 1H, Ar). Anal Calculated for C$_{27}$H$_{24}$N$_4$O$_6$·1.6H$_2$O: C, 61.27; H, 5.18; N, 10.58. Found: C, 61.29; H, 5.18; N, 10.57.

EXAMPLE 2

(s)-2-(5-(((3-Amino-1,2-dihydro-1-oxobenzo[f]quinazolin-9-yl)methyl)amino-1-oxo-2-isoindolinyl) glutaric Acid A. N-(9-Bromomethyl-1,2-dihydro-1-oxobenzo[f]quinazolin-3-yl)pivalamide N-(9-methyl-1,2-dihydro-1-oxobenzo[f]quinazolin-3-yl) pivalamide (15 g, 48 mmol) was dissolved in refluxing benzene (4000 ml). The reaction was removed from heat and N-bromosuccinimide (11.28 g, 64 mmol, Kodak) added. The solution was heated under reflux for 2 hours. Benzene was removed in vacuo, the residue slurried with a small volume of ethanol, filtered and dried under high vacuum to give the bromomethyl derivative. The product was used without further purification.

B. Diethyl(S)-2-(5-(((1,2-dihydro-1-oxo-3-pivalamidobenzo[f]quinazolin-9-yl)methyl)amino)-1-oxo-2-isoindolinyl)glutarate (S)-diethyl 2-(5-amino-1-oxo-2-isoindolinyl)glutarate (2.8 g) and N-(9-Bromomethyl-1,2-dihydro-1-oxobenzo[f]quinazolin-3-yl)pivalamide (2.0 g) were heated in dimethylformamide (15 ml) at 115° C. for 1.5 hours. The reaction mixture was concentrated onto silica gel, eluting with methylene chloride/methanol (97:3). The fractions containing product were evaporated and stored under high vacuum overnight. The partially crystallized residual oil was suspended in ethyl acetate and filtered. The solid was recrystallized from methanol, filtered and dried under high vacuum to yield the diester (0.21 g) as a white solid.

C. (S)-2-(5-(((3-Amino-1,2-dihydro-1-oxobenzo[f]quinazolin-9-yl)methyl)amino)-1-oxo-2-isoindolinyl) glutaric Acid A solution of diethyl (S)-2-(5-(((1,2-dihydro-1-oxo-3-pivalamidobenzo[f]quinazolin-9-yl)methyl)amino)-1-oxo-2-isoindolinyl)glutarate in 0.33 M aqueous sodium hydroxide/tetrahydrofuran (12 ml, 1:1) was heated to reflux. Additional water (6 ml) was added to keep the reaction mixture homogeneous, and the solution was heated under reflux for 2.5 hours. The cooled solution was adjusted to pH 3 with 1 M hydrochloric acid, the precipitate filtered off, washed with water and dried under high vacuum. The crude product, a white solid (0.15 g), contained approximately 20% of the 3-pivalamide of the desired diacid by NMR. The solid was redissolved in 0.5 M sodium hydroxide (5 ml) and stirred at room temperature for 2 days. The pH of the solution was adjusted to 2, the precipitated solid filtered off, washed with water, and dried at room temperature under high vacuum to yield the diacid as a white solid (0.13 g). $^1$H NMR (DMSO-d$_6$, 300 MHz); δ 1.88–2.08 (m, 1H), 2.10–2.30 (m, 3H), 2.26 (s, 2H), 4.52 (d, J=5.6 Hz, 2H), 4.65–4.75 (m, 1H), 6.57 (br s, 2H), 6.67–6.75 (overlapping s and dd, 2H), 7.13 br t, J=5.6 Hz, 1H), 7.27 (d, J=8.9 Hz, 1H), 7.35 (d, J=8.3 Hz, 1H), 7.46 (dd, J=8.3, 1.1 Hz, 1H), 7.85 (d, j=8.2 Hz, 1H), 8.00 (d, J=8.9 Hz, 1H), 9.68 (s, 1H), 11.14 (brs, 1H), 11.9–12.9 (v br s 2H). Anal. Calculated for C$_{28}$H$_{23}$N$_5$O$_6$·2.5H$_2$O: C, 57.61 H, 4.93; N, 12.80.

EXAMPLE 3

N-4-((1,2,5,6-Tetrahydro-3-methyl-1-oxobenzo[f] quinazolin-9-yl)-sulfonamido)benzoyl)-L-glutamic Acid A. Diethyl-N-(4-((1,2,5,6-tetrahydro-3-methyl-1-oxobenzo[f]quinazolin-9-yl)sulfonamido)benzoyl)-L-glutamate N-(4-aminobenzoyl)-L-glutamic acid diethyl ester (6.06 g, 0.0188 mole) (Aldrich) and 1,2,5,6-tetrahydro-3-methyl-1-oxobenzo[f]-quinazolin-9-sulfonyl chloride (5.84 g, 0.0188 mole) were dissolved in pyridine (55 ml) and the reaction mixture stirred at room temperature for 3.5 hours. The pyridine was removed in vacuo, the residue washed with water, and the pink solid collected by filtration. The crude product was dried under high vacuum, then subjected to chromatography on a Waters Prep 500 instrument (silica Cartridge, elution with methanol:methylene chloride (1:4). The product was recrystallized from ethanol and dried under high vacuum to yield the diethyl ester (5.68 g, 51%).

B. N-(4-((1,2,5,6-Tetrahydro-3-methyl-1-oxobenzo[f]quinazolin-9-yl)sulfonamido)benzoyl)-L-glutamic Acid Diethyl-N-(4-((1,2,5,6-tetrahydro-3-methyl-1-oxobenzo[f]quinazolin-9-yl)sulfonamido)benzoyl)-L-glutamate (4.53 g, 7.6 nunole) was dissolved in N—NaOH (64 ml) and the solution stirred at room temperature for 4 hours. The pH of the solution was adjusted to 3.00 with 1N HCl, the solid collected by filtration, washed with water and dried under high vacuum to yield the product as an off-white solid (3.94 g 96%). $^1$HNMR (DMSO-d$_6$, 300 MHz) δ: 1.84–1.96 (m, 1H, glu CH); 2.00–2.10 (m, 1H, glu CH); 2.32(s, 3H, CH$_3$, superimposed over t, 2H, glu CH$_2$); 2.71 (m, 2H, Ar CH$_2$); 2.89 (m, 2H, Ar CH$_2$); 4.28–4.36 (m, 1H, glu CH); 7.20 (d, J=9 Hz, 2H, Ar); 7.39 (d, J=8 Hz, 1H, Ar); 7.62 (dd, J=8.2 Hz, 1H, Ar); 7.74 (d, J=9 Hz, 2H, Ar); 8.44 (d, J=8 Hz, 1H, gluNH); 9.21 (d, J=2 Hz, 1H, Ar); 10.73 (s, 1H, SO$_2$NH); 12.36 (br s, 2H, CO$_2$H); 12.72 (br s, 1H, NH). Anal Calculated for C$_{25}$H$_{24}$N$_4$O$_8$S. 3/2H$_2$O: C, 52.91; H, 4.79; N, 9.87; S, 5.65. Found: C, 52.98; H, 4.78; N, 9.87; S, 5.58.

EXAMPLE 4

N-(4-(((1,2-Dihydro-3-methyl-1-oxobenzo[f] quinazolin-9-yl)methyl)amino)-2-fluorobenzoyl)-L-clutamic Acid A. Diethyl N-(4-(((1,2-Dihydro-3-methyl-1-oxobenzo[f] quinazolin-9-yl)methylamino)-2-fluorobenzoyl)-L-glutamate To a hot solution of 3,9-dimethylbenzo[f]quinazolin-1 (2H)-one (2.0 g, 8.9 mmol) in benzene (1000 ml) under nitrogen was added N-bromosuccinimide (NBS) (2.0 g, 11 mmol). The solution was stirred at reflux for 1 hour and then concentrated in vacuo to give crude 9-bromomethyl-3-methylbenzo[f]quinazolin-1(2H)-one. The solid was suspended with diethyl N-(4-amino-2-fluorobenzoyl)-L-glutamate (T. R. Jones et al., UK Patent GB 2175 903A, 1986)(6.0 g, 18 mmol) in DMF (20 ml) and stirred under nitrogen at 100° C. for 30 minutes. The reaction mixture was allowed to cool. N-methylmorpholine (1.0 ml, 9.1 mmol) (Aldrich) was added, and the solution concentrated under high vacuum. The residue was purified with silica gel chromatography eluting with methylene chloride:THF (5:1). Fractions containing product were concentrated in vacuo to a thick paste, the solid suspended in a small volume of diethyl ether, filtered under nitrogen, and dried under high vacuum to give diethyl N-(4-(((1,2-dihydro-3-methyl-1-oxobenzo[f]-quinazolin-9-yl)methyl)amino)-2-fluorobenzoyl)-L-glutamate as a white solid (2.3 g).

B. N-(4-(((1,2-Dihydro-3-methyl-1-oxobenzo[f]quinazolin-9-yl)methyl)amino)-2-fluorobenzoyl)-L-glutamic Acid A solution of diethyl N-(4-(((1,2-dihydro-3-methyl-1-oxobenzo[f]quinazolin-9-yl)methyl)amino)-2-fluorobenzoyl)-L-glutamate (2.3 g, 4.1 mmol) in ethanol (25 ml) and 0.2 N NaOH (100 ml) was stirred under nitrogen at room temperature for 3 hours. The solution was adjusted to pH 7 with 1N HCl and reduced in volume under vacuum to remove the ethanol. The product was precipitated by acidifying the solution with 1N HCl to pH 3 with stirring under nitrogen. The suspension was stirred 15 minutes, filtered under nitrogen, washed with water, pressed with a sheet of latex to remove excess water, and dried under high vacuum to give N-(4-(((1,2-dihydro-3-methyl-1-oxobenzo[f]quinazolin-9-yl)methyl)amino)-2-fluorobenzoyl)-L-glutamic acid as a white solid (2.1 g). $^1$H NMR (DMSO-$d_6$, 300 MHz) d: 1.82–2.12 (m, 2H, glu $CH_2$), 2.29 (t, J=7 Hz, 2H, glu $CH_2$), 2.43 (s, 3H, $C^3$-$CH_3$), 4.32–4.42 (m, 1H, glu CH), 4.57 (d, J=6 Hz, 2H, $C^9$-$CH_2$), 6.39 (dd, J=15.2 Hz, 1H, Ar), 6.53 (dd, J=9.2 Hz, 1H, Ar), 7.30 (t, J=6 Hz, 1H, ArNH), 7.47 (dd, J=9.9 Hz, 1H, Ar), 7.59 (d, J=9 Hz, 1H, Ar), 7.61 (dd, J=8.2 Hz, 1H, Ar), 7.73 (t, J=7 Hz, 1H, glu NH), 8.01 (d, J=8 Hz, 1H, Ar), 8.22 (d, J=9 Hz, 1H, Ar), 9.85 (s, 1H, Ar), 12.42 (br s, 2H, $CO_2H$'s), 12.53 (s, 1H, $N^2H$). Anal. Calculated for $C_{26}H_{23}FN_4O_6 \cdot 3/2\ H_2O \cdot 1/3\ NaCl$: C, 56.49: H, 4.74: N, 10.14; Cl, 2.12: Na, 1.37, Found: C, 56.48; H, 4.64; N, 10.20; Cl, 2.01; Na, 1.30.

EXAMPLE 5

The thymidylate synthase inhibitor Compound A (8 mg/kg) was lethal when administered to beagle dogs as an iv bolus for five consecutive days. In contrast Compound A at 20 mg/kg was not lethal when given as an iv bolus 30 minutes after oral administration of folic acid at 50 mg/kg. Similarly, five consecutive days of 10 mg/kg of Compound A iv was lethal when given alone. But when the same dose was given 30 minutes after an oral dose of 10, 50, 100 or 200 mg/kg of leucovorin (Wellcovorin) no deaths occurred.

EXAMPLE 6

Compound A administered as an ip bolus for five days at 3.2 or 10 mg/kg to nude mice bearing the human tumor GC3TK in the subrenal capsule produced complete inhibition of tumor growth. When 50 mg/kg of folic acid or 200 mg/kg leucovorin was administered orally 30 minutes prior to the ip bolus dose of Compound A complete inhibition of tumor growth was still observed. In another experiment, in the absence of protectant 10 mg/kg Compound A produced complete growth inhibition and 3.2 mg/kg proudced 89% inhibition. When 500 mg/kg folic acid was administered orally 30 min prior to the Compound A, tumor growth inhibition was not significantly different from that observed in the absence of the folic acid.

TABLE

Influence of Folic Acid or leucovorin upon toxicity and antitumor efficacy of Compound A

| |Folic Acid| mg/kg) | 0 | 10 | 50 | 100 | 200 | 500 |
|---|---|---|---|---|---|---|
| 10 mg/kg Compound A Dog tox. | lethal | +/− | m | m | m | m |
| bone marrow toxicity Short term: | | | | | | |
| Long term: | — | | | | | — |

TABLE-continued

Influence of Folic Acid or leucovorin upon toxicity and antitumor efficacy of Compound A

| | | | | | | |
|---|---|---|---|---|---|---|
| 10 mg/kg Compound A Mouse antitumor (% I) | >100 | | | | | >100 |
| 3.2 mg/kg Compound A Mouse antitumor (% I) | 89 | | | | | 78 |
| 10 mg/kg Compound A Mouse antitumour (% I) | >100 | | >100 | | | |
| 3.2 mg/kg Compound A Mouse antiumor (% I) | 100 | | 100 | | | |

| |leucovorin| (mg/kg) | 0 | 5 | 10 | 50 | 100 | 200 |
|---|---|---|---|---|---|---|
| 10 mg/kg Compound A Dog tox | Lethal | +/− | m | m | m | m |
| bone marrow toxicity Short term: | — | | | | | — |
| 10 mg/kg Compound A Mouse antitumor (% I) | >100 | | | | | >100 |
| 3.2 mg/kg Compound A Mouse antitumor (% I) | 100 | | | | | 100 |

Key:
— —: one animal died. one had minimal toxicity
m: minimal toxicity
—: no toxicity

What is claimed is:

1. A method of reducing toxicity associated with the administration of a therapeutically effective amount of a non-competitive thymidylate synthase inhibitor to a mammal, comprising: administering to said mammal a folate derivative selected from folic acid, 5-formyltetrahydrofolate, or 5-methyltetrahydrofolate in an amount effective to reduce said toxicity without blocking therapeutic effect of the non-competitive thymidylate synthase inhibitor, wherein the non-competitive thymidylate synthase inhibitor is a benzoquinazoline derivative of formula (I)

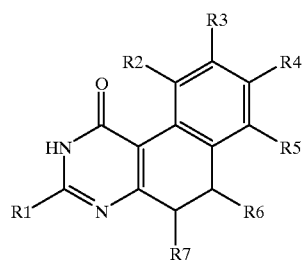

(I)

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, a group $S(O)_nR^8$ wherein n is the integer 0, 1 or 2 and $R^8$ is halo or is $C_{1-4}$ alkyl or a group $NR^9_R{}^{10}$ wherein $R^9$ and $R^{10}$ are both hydrogen, a group $NR^{11}R^{12}$ wherein $R^{11}$ and $R^{12}$ are the same or different and each is hydrogen or $C_{1-4}$ alkyl, a group $OR^{13}$ wherein $R^{13}$ is hydrogen or $C_{1-4}$ alkyl optionally substituted by halo, a $C_{1-4}$ aliphatic group optionally substituted by a group $OR^{14}$ or $NR^{14}R^{15}$ where $R^{14}$ and $R^{15}$ are the same or different and each is hydrogen or $C_{1-4}$ alkyl; or two of $R^2$ to $R^5$ are linked together to form a benzo group, or one of $R^2$ to $R^5$ is a group —X—Y—$R^{16}$ wherein X is $CH_2$, $NR^{17}$, CO or $S(O)_m$ and m is 0, 1 or 2 and $R^{17}$ is hydrogen or a $C_{1-4}$ aliphatic group and Y is $CH_2$, $NR^{17'}$, O, or $S(O)_{m'}$ wherein m' is 0,1 or 2 and $R^{17'}$ is hydrogen or a $C_{1-4}$ aliphatic group provided that X and Y are only the same when each is $CH_2$, or —X—Y— is a group —O—, —$NR^{17}$—, —CH=CH— or —N=N— wherein $R^{17}$ is as hereinbefore defined, $R^{16}$ is a $C_{1-4}$ aliphatic group or a 5- or 6-membered aromatic ring optionally substituted by a group $R^{18}$ at a position at least one carbon atom removed from that linked to Y, the 5- or 6-membered ring being optionally further substituted by a halo atom; and $R^{18}$ is halo, $C_{1-4}$ alkoxy, nitro, nitrile, $C_{1-4}$ alkyl optionally substituted by halo, halo or a group $COR^{19}$ wherein $R^{19}$ is hydroxy, $C_{1-4}$ alkoxy or $C_{1-6}$ alkyl optionally substituted by one or two carboxyl groups or $C_{1-12}$ esters thereof or $R^{19}$ is a group $NR^{20}R^{21}$ wherein $R^{20}$ and $R^{21}$ are the same or different and each is hydrogen or $C_{1-4}$ alkyl optionally substituted by hydroxy or $R^{19}$ is an amino acid group or an ester thereof in which the first nitrogen atom of the amino acid group may be linked to the 5- or 6-membered aromatic ring to form a further 5- or 6-membered heterocyclic ring or $R^{19}$ is an $C_{2-3}$ alkylene group linked to the 5- or 6-membered aromatic ring to form a further 5- or 6-membered ring;

$R^6$ and $R^7$ are the same or different and each is hydrogen, $C_{1-4}$ alkyl optionally substituted by hydroxy or $C_{1-4}$ alkoxy, or methyl substituted by bromo, or together form a benzo group;

provided that at least one of $R^2$ to $R^7$ is other than hydrogen and that $R^4$ is not methoxy when $R^1$ is hydroxy or methyl.

2. The method according to claim 1 wherein the benzoguinazoline derivative is a compound of formula (III)

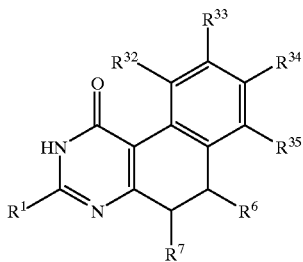

or a salt thereof wherein R1, R6 and R7 are as hereinbefore defined and R32 to R35 are the same or different and one is a group —X—Y—R16 and the others are the same or different and each is selected from hydrogen, halo, nitro, a group S(O)nR8, a group NR11R12, a group OR13 or a C1–4 aliphatic group optionally substituted by a group OR14 or NR14R15, wherein X, Y, R8, R11, R12, R13, R14, R15 and R16 are as hereinbefore defined.

3. The method according to claim 2 wherein the benzoguinazoline derivative is selected from:

(S)-2-5-(((1,2-dihydro-3-methyl-1-oxobenzo[f]quinazolin-9-yl)methyl)amino)-1-oxo-2-isoindolinyl) glutaric acid;

N-(4-(((1,2-dihydro-3-methyl-1-oxobenzo[f]quinazolin-9-yl)methyl)amino)-2-fluorobenzoyl)-L-glutamic acid;

N-(4-(((1,2,5,6-tetrahydro-3-methyl-1-oxobenzo[f]quinazolin-9-yl)sulfonamido)benzoyl)-L-glutamic acid;

or salts thereof.

4. The method according to claim 1 wherein the benzoguinazoline derivative is a compound of the formula (IV)

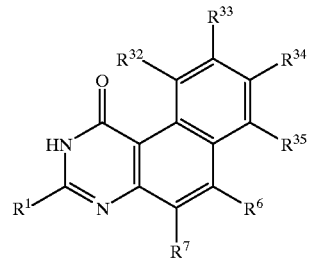

or a salt thereof, wherein R1, R6, R7 and R32 to R35 are as hereinbefore defined.

5. The method according to claim 1 wherein the folate derivative is folic acid and the benzoguinazoline derivative is (S)-2-(5-(((1,2-dihydro-3-methyl-1-oxobenzo[f]quinazolin-9-yl)methyl)amino)-1-oxo-2-isoindolinyl) glutaric acid.

6. A method according to claim 1 wherein said folate derivative is administered either before, concurrently with, or after the administration of said benzoquinazoline derivative.

7. A method according to claim 1 wherein said folate derivative is administered in a dose of from 1 mg/kg bodyweight to 300 mg/kg bodyweight.

8. A method according to claim 1 wherein said folate derivative is administered in a dose of from 5 mg/kg bodyweight to 50 mg/kg bodyweight.

9. A method according to claim 1 where said toxicity is intestinal toxicity.

10. A method of treating susceptible neoplastic growth, comprising:

administration of (i) a therapeutically effective amount of a non-competitive thymidylate inhibitor wherein the non-competitive thymidylate synthase inhibitor is a benzoquinazoline derivative of formula (I)

(I)

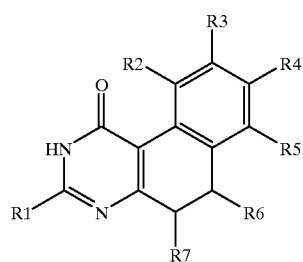

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, a group $S(O)_nR^8$ wherein n is the integer 0, 1 or 2 and $R^8$ is halo or is $C_{1-4}$ alkyl or a group $NR^9R^{10}$ wherein $R^9$ and $R^{10}$ are both hydrogen, a group $NR^{11}R^{12}$ wherein $R^{11}$ and $R^{12}$ are the same or different and each is hydrogen or $C_{1-4}$ alkyl, a group $OR^{13}$ wherein $R^{13}$ is hydrogen or $C_{1-4}$ alkyl optionally substituted by halo, a $C_{1-4}$ aliphatic group optionally substituted by a group $OR^{14}$ or $NR^{14}R^{15}$ wherein $R^{14}$ and $R^{15}$ are the same or different and each is hydrogen or $C_{1-4}$ alkyl; or two of $R^2$ to $R^5$ are linked together to form a benzo group, or one of $R^2$ to $R^5$ is a group —X—Y—$R^{16}$ wherein X is $CH_2$, $NR^{17}$, CO or $S(O)_m$ and m is 0, 1 or 2 and $R^{17}$ is hydrogen or a $C_{1-4}$ aliphatic group and Y is $CH_2$, $NR^{17'}$, O, or $S(O)_{m'}$ wherein m' is 0,1 or 2 and $R^{17'}$ is hydrogen or a $C_{1-4}$ aliphatic group provided that X and Y are only the same when each is $CH_2$, or —X—Y— is a group —O—, —$NR^{17}$—, —CH=CH— or —N=N— wherein $R^{17}$ is as hereinbefore defined, $R^{16}$ is a $C_{1-4}$ aliphatic group or a 5- or 6-membered aromatic ring optionally substituted by a group $R^{18}$ at a position at least one carbon atom removed from that linked to Y, the 5- or 6-membered ring being optionally further substituted by a halo atom; and $R^{18}$ is halo, $C_{1-4}$ alkoxy, nitro, nitrile, $C_{1-4}$ alkyl optionally substituted by halo, halo or a group $COR^{19}$ wherein $R^{19}$ is hydroxy, $C_{1-4}$ alkoxy or $C_{1-6}$ alkyl optionally substituted by one or two carboxyl groups or $C_{1-12}$ esters thereof or $R^{19}$ is a group $NR^{20}R^{21}$ wherein $R^{20}$ and $R^{21}$ are the same or different and each is hydrogen or $C_{1-4}$ alkyl optionally substituted by hydroxy or $R^{19}$ is an amino acid group or an ester thereof in which the first nitrogen atom of the amino acid group may be linked to the 5- or 6-membered aromatic ring to form a further 5- or 6-membered heterocyclic ring or $R^{19}$ is an $C_{2-3}$ alkylene group linked to the 5- or 6-membered aromatic ring to form a further 5- or 6-membered ring;

$R^6$ and $R^7$ are the same or different and each is hydrogen, $C_{1-4}$ alkyl optionally substituted by hydroxy or $C_{1-4}$ alkoxy, or methyl substituted by bromo, or together form a benzo group;

provided that at least one of $R^2$ to $R^7$ is other than hydrogen and that $R^4$ is not methoxy when $R^1$ is hydroxy or methyl; and (ii) a folate derivative selected from folic acid, 5-formyltetrahydrofolate, or 5-methyltetrahydrofolate in an amount effective to reduce toxicity of the benzoquinazoline derivative without blocking the therapeutic effect of the benzoquinazoline derivative, to a mammal.

11. A treatment combination for treating susceptible neoplastic growth, comprising, i) a therapeutically effective amount of a non-competitive thymidylate synthase inhibitor wherein the non-competitive thymidylate synthase inhibitor is a benzoquinazoline derivative of formula (I)

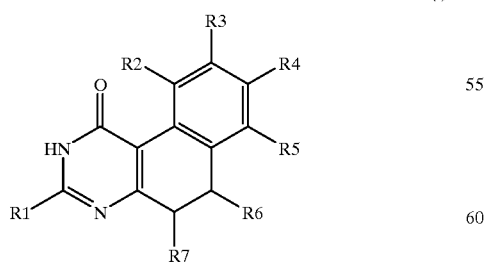

(I)

or a salt thereof, wherein the dotted line represents a single or double bond, $R^1$ is $C_{1-4}$ alkyl or amino optionally substituted by a $C_{1-4}$ alkyl, $C_{1-5}$ alkanoyl or benzyl group;

$R^2$, $R^3$, $R^4$ and $R^5$ are the same or different and each is selected from hydrogen, phenyl, halo, nitro, a group $S(O)_n R^8$ wherein n is the integer 0, 1 or 2 and $R^8$ is halo or is $C_{1-4}$ alkyl or a group $NR^9R^{10}$ wherein $R^9$ and $R^{10}$ are both hydrogen, a group $NR^{11}R^{12}$ wherein $R^{11}$ and $R^{12}$ are the same or different and each is hydrogen or $C_{1-4}$ alkyl, a group $OR^{13}$ wherein $R^{13}$ is hydrogen or $C_{1-4}$ alkyl optionally substituted by halo, a $C_{1-4}$ aliphatic group optionally substituted by a group $OR^{14}$ or $NR^{14}R^{15}$ wherein $R^{14}$ and $R^{15}$ are the same or different and each is hydrogen or $C_{1-4}$ alkyl; or two of $R^2$ to $R^5$ are linked together to form a benzo group, or one of $R^2$ to $R^5$ is a group —X—Y—$R^{16}$ wherein X is $CH_2$, $NR^{17}$, CO or $S(O)_m$ and m is 0, 1 or 2 and $R^{17}$ is hydrogen or a $C_{1-4}$ aliphatic group and Y is $CH_2$, $NR^{17'}$, O, or $S(O)_{m'}$ wherein m' is 0,1 or 2 and $R^{17'}$ is hydrogen or a $C_{1-4}$ aliphatic group provided that X and Y are only the same when each is $CH_2$, or —X—Y— is a group —O—, —$NR^{17}$—, —CH=CH— or —N=N— wherein $R^{17}$ is as hereinbefore defined, $R^{16}$ is a $C_{1-4}$ aliphatic group or a 5- or 6-membered aromatic ring optionally substituted by a group $R^{18}$ at a position at least one carbon atom removed from that linked to Y, the 5- or 6-membered ring being optionally further substituted by a halo atom; and $R^{18}$ is halo, $C_{1-4}$ alkoxy, nitro, nitrile, $C_{1-4}$ alkyl optionally substituted by halo, halo or a group $COR^{19}$ wherein $R^{19}$ is hydroxy, $C_{1-4}$ alkoxy or $C_{1-6}$ alkyl optionally substituted by one or two carboxyl groups or $C_{1-12}$ esters thereof or $R^{19}$ is a group $NR^{20}R^{21}$ wherein $R^{20}$ and $R^{21}$ are the same or different and each is hydrogen or $C_{1-4}$ alkyl optionally substituted by hydroxy or $R^{19}$ is an amino acid group or an ester thereof in which the first nitrogen atom of the amino acid group may be linked to the 5- or 6-membered aromatic ring to form a further 5- or 6-membered heterocyclic ring or $R^{19}$ is an $C_{2-3}$ alkylene group linked to the 5- or 6-membered aromatic ring to form a further 5- or 6-membered ring;

$R^6$ and $R^7$ are the same or different and each is hydrogen, $C_{1-4}$ alkyl optionally substituted by hydroxy or $C_{1-4}$ alkoxy, or methyl substituted by bromo, or together form a benzo group;

provided that at least one of $R^2$ to $R^7$ is other than hydrogen and that $R^4$ is not methoxy when $R^1$ is hydroxy or methyl; and (ii) a folate derivative selected from folic acid, 5-formyltetrahydrofolate, or 5-methyltetrahydrofolate in an amount effective to reduce toxicity of the benzoquinazoline derivative without blocking the therapeutic effect of the benzoquinazoline derivative.

* * * * *